United States Patent [19]

Hart et al.

[11] 3,970,584

[45] July 20, 1976

[54] AEROSOL PACKAGE CONTAINING A FOAM-FORMING EMULSION AND PROPELLENT SYSTEM

[75] Inventors: John W. Hart; Thomas C. Rolfson, both of Racine, Wis.

[73] Assignee: S. C. Johnson & Son, Inc., Racine, Wis.

[22] Filed: Feb. 14, 1973

[21] Appl. No.: 332,534

[52] U.S. Cl. ............................ 252/305; 252/90; 252/307; 252/DIG. 13; 424/45; 424/47; 424/60; 424/73; 424/DIG. 10; 424/DIG. 13
[51] Int. Cl.² ........................................... C09K 3/30
[58] Field of Search ............... 424/47, 45; 252/305, 252/90

[56] References Cited

UNITED STATES PATENTS

| | | | |
|---|---|---|---|
| 2,978,422 | 4/1961 | Meister | 252/305 X |
| 3,092,555 | 6/1963 | Horn | 252/305 X |
| 3,370,014 | 2/1968 | Reich et al. | 252/305 X |
| 3,387,425 | 6/1968 | Flanner | 252/305 X |

*Primary Examiner*—Richard D. Lovering

[57] ABSTRACT

An aerosol package containing a foam-forming, oil-in-water emulsion and a propellent system consisting essentially of nitrous oxide and a liquefied, normally gaseous hydrocarbon or halogenated hydrocarbon is described. The emulsion upon being dispensed is a unique, rich, shiny, creamy foam having good foam density and stiffness characteristics.

5 Claims, No Drawings

AEROSOL PACKAGE CONTAINING A FOAM-FORMING EMULSION AND PROPELLANT SYSTEM

The present invention is directed to an aerosol package containing a foam-forming emulsion and a propellant system. More particularly, the invention is directed to an aerosol package containing a foam-forming, oil-in-water emulsion (which includes a foam-forming ingredient) and a propellant system consisting essentially of two types of gaseous ingredients: one being liquifiable under conditions known in the aerosol art, and the other being not readily liquifiable.

Numerous compositions to be dispensed as foams have been packaged in aerosol packages. Exemplary compositions include shaving creams and lathers, floor and automobile cleaning and polishing compositions, and food products such as whipped cream, cheese spreads, mayonnaise, and the like. In these compositions, some of which include aqueous emulsions, various propellants have been used to meet essential characteristics of the product or safety requirements. The known propellants include the liquefiable gases such as unsubstituted and halogen-substituted hydrocarbons and the gases which are not easily liquified (compressible) such as nitrous oxide, carbon dioxide, and nitrogen.

Certain products, including hand and body lotions, are utilized as foams for the proper feel and appearance. A particularly pleasing effect or feel is obtained, however, if such products are dispensed as rich, slightly wet, creamy foams. These foam properties generally require a foam with a fine bubble texture. Due to the unique characteristics of foams needed for hand and body lotions, it has been difficult to provide a completely acceptable aerosol package containing such lotions. The difficulty is due in substantial part to the shortcomings of known propellants. Using the known propellents, it has been found that the foam obtained upon being dispensed from an aerosol package is either too wet and runny with limited foam stability or too stiff and dry which only dissipates slowly with rubbing— neither of which provides the essential pleasant feel and appearance.

Accordingly, a primary object of this invention is to provide an improved aerosol package containing a composition which upon dispensing will produce a rich, shiny creamy foam having a fine or delicate bubble structure. A further object of this invention is to provide an aerosol package containing a foam-forming, oil-in-water emulsion particularly suited, as a result of its foam characteristics, for those products which are desirably dispensed as foams. A further object of this invention is to provide an aerosol package containing foam-forming, oil-in-water emulsion and a propellant system consisting essentially of a compressible gas and a liquefied gas. Another object of this invention is to provide a propellant system for use in an aerosol package with an oil-in-water emulsion containing a foam-forming ingredient, said propellant system dispensing the emulsion from the package as a stable foam having a rich, shiny, creamy appearance. Other objects of this invention will appear herein.

These and other objects are attained by the practice of this invention, at least one embodiment of which comprises providing an aerosol package containing a foam-forming, oil-in-water emulsion and a propellant system consisting essentially of nitrous oxide and a liquefied, normally gaseous hydrocarbon or halogenated hydrocarbon. Such emulsions upon being dispensed provide a rich, shiny, creamy foam having a fine or delicate bubble structure and good foam density and stiffness characteristics. Neither of the two members of the propellant system when used alone will provide equivalent results.

More specifically, it has been found that a propellant system consisting essentially of nitrous oxide and a liquified, normally gaseous hydrocarbon or halogenated hydrocarbon when used within certain select ratios to dispense a foam-forming, oil-in-water emulsion from an aerosol package will provide a foam having unique and optimum characteristics desirable for a personal care product. The foam will have a fine or delicate bubble structure; good density and stiffness characteristics; and will be rich, shiny and creamy, providing a desirable and pleasant feeling when applied to the skin. The foam so dispensed will retain its integrity and remain stable until spread on the skin whereupon it rapidly dissipates.

The aforesaid characteristics are particularly surprising because nitrous oxide alone with the same oil-in-water emulsion provides a limited foam structure which quickly breaks down to a watery consistency. The hydrocarbon or halogenated hydrocarbon propellant alone, while forming a foam, produces a stiff, dry, dull body which does not have the pleasing appearance or soothing feeling of a lotion and will not dissipate easily when worked with the fingers.

To obtain the desired objects of this invention, the weight ratio of nitrous oxide to hydrocarbon or halogenated hydrocarbon must be from about 2:1 to about 1:1.5. For example and based on a 142-grams of a foam-forming, oil-in-water emulsion, the propellant system consists essentially of from about 1.0–3.5 grams of nitrous oxide and from about 0.5–4.0 grams of hydrocarbon or halogenated hydrocarbon, and preferably from about 1.4–3.5 grams hydrocarbon or halogenated hydrocarbon and 1.5–2.4 grams nitrous oxide. If too much hydrocarbon or halogenated hydrocarbon or if too little nitrous oxide is employed in the propellant system, the foam tends to be stiff, dry, and dull in appearance, without the pleasing feeling and appearance associated with a rich, creamy, fine-textured foam. Using too little liquified gas and/or excess nitrous oxide results in a wet, watery foam which breaks down too easily.

The above ratios and the total amount of propellant are dependant to some extent upon the particular oil-in-water emulsion employed and the intended use of such emulsion.

Although it is not desired or intended to be limited by a theoretical explanation why the present combination provides the improved characteristics, it is believed that the compressible gas functions as the propelling force to dispense the product and, in the case of nitrous oxide, is soluble in the aqueous phase; and the liquified gas is solubilized in the oil phase and "puffs" up the product as it is dispensed. Being soluble in the oil phase, the latter propellant is held therein until spread on the skin or rubbed out. In any event, the combination of propellants within the disclosed ratios is essential to provide the desired foam characteristics described above.

The present invention, while being described primarily in reference to a hand or body lotion, applies to any oil-in-water emulsion which contains a foam-forming ingredient where the aforesaid foam characteristics may be desirable, i.e., a rich, creamy, shiny foam. These products include shaving aids, insect repellents, facial cleansers, sun tan lotions, toothpaste, food products (such as toppings, mayonnaise, whipped cream, and cheese spreads), pharmaceutical preparations, and the like. It is only essential that the product to be dispensed comprise an oil-in-water emulsion and include therein a foam-forming ingredient.

It has been found that any oil-in-water emulsion comprising a foam-forming or holding matrix (such as various soap systems comprising fatty acids, fatty alcohols, or wax-type matrices emulsified into a continuous water phase with an anionic, non-ionic, or cationic surfactant) can be utilized.

Some examples of anionic synthetic detergents include, but are not limited to, soaps such as triethanolamine, sodium and/or potassium stearates; alkyl alkoxylated phosphates, alkyl aryl sulfonates and alkyl sulfates; specifically, sodium lauryl sulfate and alkyl dodecylbenzene sodium sulfonate.

Nonionic synthetic detergents which are suitable for forming foam in the present compositions include polyalkoxylated long-chain fatty acids and alcohols and esters thereof. Specifically, suitable materials include polyoxyethylene stearate and oleate, polyethoxylated cetyl alcohol, the mono-, di- and tri- esters of various polyols, glycerol monostearate, sorbitan tristearate and sorbitan dioleate.

Various cationic synthetic detergents are also suitable in practicing the present invention. This category, as is well known, includes compositions such as n-alkyl trimethyl ammonium chloride, di-coco dialkyl ammonium chloride, stearyl dimethyl benzyl ammonium and cetyl dimethyl benzyl ammonium chloride.

In addition to the synthetic detergent, a fatty or waxy material may sometimes be used in combinations therewith to serve the foam-forming function. Examples of such materials are free fatty acids, fatty alcohols, and other well-known bodying agents such as polyolefin waxes and waxes of vegetable or mineral origin.

As will be appreciated by one skilled in the art, the foam-forming ingredient and/or matrix for holding the foam-forming ingredient will be varied depending upon the intended use of the emulsion. Thus, a particular system can function as a carrier for a variety of active components for dispensing as a rich, creamy foam which is rapidly dissipated when spread on the skin. Examples of these are topical analgesics such as methyl salicylate, topical anesthetics such as ethyl p-aminobenzoate, ultra-violet light absorbers such as p-aminobenzoic acid, menthol or camphor decongestants, moisturizing lotions with emollients such as lanolin, cleansing creams with mineral oil and the like.

As used herein, "liquefied, normally gaseous" designates a material which is gaseous at room temperature and atmospheric pressure, but which is readily liquefied at the pressure normally employed in pressure packaging.

The liquefied, normally gaseous hydrocarbon or halogenated hydrocarbon component of the propellant system utilized in this invention can be any of the known such propellants having 1–5 carbon atoms or mixtures thereof. Preferred liquefied hydrocarbon propellants include the saturated aliphatic hydrocarbons such as methane, ethane, n-propane, n-butane, isobutane, n-pentane and isopentane. Preferred liquefied halogenated hydrocarbons include dichlorodifluoroethane, dichlorotetrafluoroethane, dichlorodifluoromethane, trichloromonofluoromethane, dichloromonofluoromethane, methylene chloride, vinyl chloride, octafluorocyclobutane, and chloropentafluoroethane. Mixtures of two or more of these propellants can be used.

The foams produced by this invention have a density from about 0.10 to about 0.18 g/cc and preferably from about 0.12 to about 0.17 g/cc and a stiffness from about 240 to 350 grams/square centimeter and preferably from about 260 to about 325 grams/square centimeter. Foam density data as set forth in Table I below was obtained by discharging, under static conditions, sufficient foam to fill levelfull a weighed smooth-top beaker of known volume. The weight of the filled beaker was established and the density calculated. Foam stiffness was measured using a Universal Testing Instrument — Model TTC manufactured by Instron Engineering Corporation of Boston, Mass. A special attachment was constructed which consists of a plastic cylinder of approximately 8 inches in length and has an inside diameter of 3 inches. This cylinder is mounted vertically on a compression cell having a maximum rating of 2,000 grams. A plunger or piston is constructed of a plexiglass circular plate mounted to an aluminum rod. The diameter of the piston is 2⅞ inches. The piston is mounted to the crosshead of the instrument and is designed to fit inside the cylinder. The difference between the inside area of the cylinder and the area of the piston is calculated to be 3.72 square inches. Approximately two-thirds of the cylinder is filled with the product to be tested and the piston is forced through the product. The force required to push the piston through the material is recorded on a chart. The maximum force required on the initial pass through the material is designated as "foam stiffness."

The values at which the instrument was set for the evaluation of these foams are listed as follows:

| | |
|---|---|
| Time (initial-terminal) | 30 minutes |
| Chart speed | 0.2" per minute |
| Full scale reading | 2,000 grams |
| Cross-head speed | 1.0 |
| Cycle length | 1 inch from bottom to 3" from bottom |
| Shaking procedure | 1 minute on "Atlab shaker" |
| Cycle control | Extension |
| Gear | High |

The calculations to determine stiffness and density are as follows:

$$\text{Stiffness} = \frac{\text{Force of initial pass}}{3.72 \text{ sq. in.}}$$

$$\text{Foam density} = \frac{\text{Weight of foam}}{\text{Volume of container}}$$

The aerosol containers which can be used to package the foam-forming, oil-in-water emulsions of this invention can be any of the conventional aerosol containers. The details and mechanical features of these containers are well-known and need not be detailed herein.

This invention will be further illustrated by the following examples of preferred embodiments. However, it will be understood that these examples are included for purposes of illustration and are not intended to limit the scope of this invention.

Example I demonstrates the critical characteristics of the propellant system of this invention. In this example, foam characteristics are established for nitrous oxide alone, isobutane alone, nitrous oxide-isobutane and nitrous oxide-halogenated hydrocarbon combinations, and hydrocarbon mixtures containing isobutane, and other low-molecular weight hydrocarbons. Examples II–VI illustrate the criticality of the propellant system in specific working embodiments of this invention.

EXAMPLE I

An oil-in-water emulsion useful as a hand and body lotion is prepared as follows:

|   |   |   |
|---|---|---|
| A | Stearic Acid | 4.00 g. |
|   | Sorbitan Tristearate | 0.50 g. |
|   | Cetyl Alcohol | 0.50 g. |
|   | Isopropyl Myristate | 0.50 g. |
|   | Fatty acid diester of a coconut oil derived polyol | 1.00 g. |
|   | Lanolin alcohols | 2.50 g. |
|   | Propyl p-hydroxybenzoate | 0.05 g. |
|   | Talc | 2.00 g. |
|   | Deionized water | 85.45 g. |
|   | 70% Sorbitol | 2.00 g. |
| B | Triethanolamine | 1.00 g. |
|   | Sodium lauryl sulfate | 0.25 g. |
|   | Methyl p-hydroxybenzoate | 0.10 g. |
| C | Fragrance | 0.15 g. |
|   |   | 100.00 |

The ingredients of part A are mixed together and heated to 170°F. The ingredients of part B are mixed together and heated to 170°F. A is then added to B with mild agitation, and mild stirring continues for 10 minutes before force cooling to 120°F. At 120°F. the fragrance C is added with mild agitation and the composition force cooled to 100°F.

142-gram samples (1–12) of the above oil-in-water emulsion are charged to 6 oz. aerosol containers. The container is fixed with a foam-type valve utilizing a 4-inch polyethylene dip tube. After charging the 142 grams of emulsion into each can, the valve is vacuum crimped and the designated amount of isobutane is filled into each can through the dip tube. Thereafter, the can is transferred to a "gasser-shaker" and pressurized with nitrous oxide at 100 pounds line pressure until the desired amount of nitrous oxide is added. The cans are then placed in a hot tank at 130°F. for three minutes. Thereafter the cans are allowed to cool slowly to room temperature.

The gasser-shaker referred to above comprises an electric motor attached to a gear box which rotates a circular plate. At the perimeter of the plate is a pin which is attached to an apparatus which holds the aerosol container and also contains a filling device for propellant insertion. As the cylinder rotates, the pin on the perimeter transfers an irregular movement to the can-filling apparatus producing a shaking effect which allows the propellant to be filled in an effective manner. As will be appreciated by one skilled in the art, other methods of manufacture such as in-line blending of emulsion and propellants or sparging the nitrous oxide may be used.

In Tables I, II, III, and IV, the foams are rated subjectively by dispensing a small quantity of product onto the palm of the hand and spreading to observe the foam structure, shininess, whiteness, creaminess and viscosity. Each sample is given one of the following ratings:

E  Excellent — very rich and creamy in appearance, does not show any bubble structure or shows a very fine (small) bubble structure; does not rapidly become dull; upon spreading on the skin it retains its creaminess and does not lose viscosity or appear watery.

G  Good — rich and creamy in appearance, very small bubble size, "dulls" more rapidly than an excellent foam, retains creaminess upon spreading on the skin, and does not become watery.

FG  Fairly Good — a moderate amount of creaminess noticeable, bubble structure is noticeable; upon spreading on the skin the product dulls rapidly and becomes somewhat lower in apparent viscosity.

F  Fair — very little creaminess noticeable, larger bubble structure than a "fairly good" foam, upon spreading on the skin it becomes thin in appearance and watery.

P  Poor — no creaminess noticeable, large bubble structure, and when spread on the skin it becomes very thin and watery in appearance.

VP  Very Poor — dry foam, large very dull bubbles, difficult to spread on the skin.

Samples 1–12, as to composition and properties, are set forth in Table I. In addition, In Table I, the products are rated by the more objective measurements of foam density and stiffness.

TABLE I

| Sample No. | Propellant System (g.) |  | Subjective Rating of Foam | Foam Density (g/cc) | Foam Stiffness (g/cc) |
|---|---|---|---|---|---|
| 1 | isobutane | (1.4) | VP | .10 | 360 |
| 2 | isobutane | (7.1) | VP | .07 | 372 |
| 3 | nitrous oxide | (2.2) | P | .32 | 225 |
| 4 | isobutane nitrous oxide | (1.4) (1.8) | E | .16 | 258 |
| 5 | isobutane nitrous oxide | (2.1) (1.7) | G | .13 | 310 |
| 6 | isobutane nitrous oxide | (2.8) (1.6) | G | .12 | 354 |
| 7 | 83% isobutane/ 17% propane nitrous oxide | (1.4) (1.6) | E | .15 | 295 |
| 8 | n-butane nitrous oxide | (1.4) (2.1) | G | .16 | 280 |
| 9 | 55% isobutane/ |  | G | .12 | 320 |

TABLE I-continued

| Sample No. | Propellant System (g.) | | Subjective Rating of Foam | Foam Density (g/cc) | Foam Stiffness (g/cc) |
|---|---|---|---|---|---|
| | 45% Propellant 12* | (2.8) | | | |
| | nitrous oxide | (1.7) | | | |
| 10 | isobutane | (1.4) | P | .29 | 169 |
| | nitrogen | (0.5) | | | |
| 11 | isobutane | (1.4) | P | .20 | 220 |
| | carbon dioxide | (2.6) | | | |
| 12 | Propellant 12 | (1.4) | P | .21 | 220 |
| | nitrous oxide | (1.9) | | | |

*Propellant 12 is dichlorodifluoroethane.

As seen from the data of Table I, isobutane alone (samples 1 and 2) and nitrous oxide alone (sample 3) do not provide satisfactory foams. However, the combination of Propellant 12 and isobutane with nitrous oxide (sample 9) and the combination of an unsubstituted hydrocarbon and nitrous oxide (samples 4–8) give results rated as ranging from good to excellent.

EXAMPLE II

A shaving cream having the following formulation is charged in an aerosol container using the indicated propellant system:

| | | |
|---|---|---|
| A. | 70% Sorbitol | 7.7 g. |
| | Deionized H$_2$O | 60.3 g. |
| B. | Triethanolamine (85%) | 3.9 g. |
| | Deionized H$_2$O | 5.1 g. |
| C. | Palmitic Acid | 7.3 g. |
| | Isopropyl Myristate | 2.8 g. |
| D. | Fragrance | 0.2 g. |
| E. | Propylene Glycol | 12.7 g. |
| | | 100.0 g. |

Heat A with agitation to 190°F. Charge B with mild agitation. Charge C at 200°F. to A and B. Force cool to 100°F. and charge D. Continue cooling to 90°F. and add E. 150 grams of the emulsion was charged to each of seven individual 6 oz. aerosol containers and pressurized. The samples were then subjectively evaluated as shown in Table II.

TABLE II

| Sample No. | Propellant System (g.) | | Subjective Rating of Foam |
|---|---|---|---|
| | N$_2$O | Isobutane | |
| 13 | 2.10 | — | P |
| 14 | — | 5.80 | VP |
| 15 | 2.23 | 0.58 | F |

TABLE II-continued

| Sample No. | Propellant System (g.) | | Subjective Rating of Foam |
|---|---|---|---|
| | N$_2$O | Isobutane | |
| 16 | 2.34 | 1.20 | G |
| 17 | 2.09 | 1.70 | G |
| 18 | 2.20 | 2.40 | F |
| 19 | 2.25 | 2.90 | VP |

EXAMPLE III

A lady's facial cream having the following formulation is charged with the indicated propellant system:

| | | |
|---|---|---|
| A. | 70% Sorbitol | 7.6 g. |
| | Deionized Water | 53.3 g. |
| B. | Triethanolamine (85%) | 4.2 g. |
| | Deionized Water | 4.2 g. |
| C. | Palmitic Acid | 6.9 g. |
| | Isopropyl Myristate | 0.5 g. |
| | Polyethylene Glycol M.W. 600 | 1.0 g. |
| D. | Fragrance | 0.2 g. |
| E. | Deionized Water | 10.0 g. |
| | Propylene Glycol | 2.0 g. |
| F. | Isopropyl Myristate | 6.9 g. |
| | Mineral Oil 70 Viscosity | 2.5 g. |
| | Propylene Glycol | 0.7 g. |
| | | 100.0 g. |

Heat A, B, C individually to 180°F. Add B to A with stirring. Add C to AB with stirring. Force cool to 100°F. in a cooling bath. Add D and continue to cool to 82°F. before adding E with stirring. Heat to 92°F. with continued stirring for 10 minutes. Add F and mix for 5 minutes.

150 grams of the emulsion was charged to each of nine individual 6 oz. aerosol containers, pressurized, and subjectively evaluated as shown in Table III.

TABLE III

| Sample No. | Propellant System (g.) | | Subjective Rating of Foam |
|---|---|---|---|
| 20 | Propellant 12 | (11.5) | VP |
| 21 | Propellant 12 | (7.3) | VP |
| | Propellant 114* | (9.7) | |
| 22 | 75% Propellant 114/25% Propellant 12 | (3.7) | E |
| | nitrous oxide | (2.4) | |
| 23 | nitrous oxide | (2.4) | P |
| 24 | isobutane | (5.8) | VP |
| 25 | isobutane | (.58) | G |
| | nitrous oxide | (2.2) | |
| 26 | isobutane | (1.2) | G |
| | nitrous oxide | (2.1) | |
| 27 | isobutane | (1.7) | FG |
| | nitrous oxide | (2.0) | |
| 28 | isobutane | (2.4) | F |
| | nitrous oxide | (2.0) | |
| 29 | isobutane | (2.9) | FG |

TABLE III-continued

| Sample No | Propellant System (g.) | Subjective Rating of Foam |
|---|---|---|
| | nitrous oxide (2.0) | |

*Propellant 114 is dichlorotetrafluoroethane.

EXAMPLE IV

A shampoo having the following formulation is charged with the indicated propellant system:

| | | |
|---|---|---|
| A | Triethanolamine Lauryl Sulfate | 35.5 g. |
| | Triethanolamine salt of peptide coco fatty acid condensate | 16.9 g. |
| | Deionized Water | 36.5 g. |
| | Isopropyl Myristate | 2.0 g. |
| | Glycerol Monoisostearate | 0.5 g. |
| | Triethanolamine 99% | 1.1 g. |
| B | Propylene Glycol | 1.1 g. |
| | Oleyl Sarcosine | 2.1 g. |
| | Super diethanolamide of lauryl acid | 3.8 g. |
| | Fragrance | 0.5 g. |
| | | 100.0 g. |

Heat B above to 160°F. and add A thereto with stirring and agitate for 10 minutes. Permit to cool.

150 grams of the emulsion was charged to each of eight individual 6 oz. aerosol containers, pressurized, and subjectively evaluated as shown in Table IV.

TABLE IV

| Sample No. | Propellant System (g.) | Subjective Rating of Foam |
|---|---|---|
| 30 | Propellant 12 (11.5) | P |
| 31 | Propellant 114 (9.7) | VP |
| 32 | nitrous oxide (2.9) | P |
| 33 | isobutane (5.8) | P |
| 34 | isobutane (.58) nitrous oxide (2.74) | G |
| 35 | isobutane (1.2) nitrous oxide (2.75) | E |
| 36 | isobutane (1.7) nitrous oxide (2.86) | G |
| 37 | isobutane (2.4) nitrous oxide (2.32) | FG |
| 38 | isobutane (2.9) nitrous oxide (2.65) | F |

In Examples V through IX below, several different types of personal care products were formulated containing the components in the amounts set forth. In each instance 150 grams of each product was charged to a 6 oz. aerosol container, pressurized in the same manner described in Example I, sample 4, to produce an excellent foam.

EXAMPLE V

A sun tan lotion was prepared having the following formulations:

| | | |
|---|---|---|
| A | Stearic Acid | 4.0 g. |
| | Sorbitan Tristearate | 0.5 g. |
| | Cetyl Alcohol | 0.5 g. |
| | Mineral Oil 70 Viscosity | 7.0 g. |
| | Lanolin Alcohols | 2.5 g. |
| | Propyl p-hydroxybenzoate | 0.1 g. |
| | Deionized Water | 76.9 g. |
| | 70% Sorbitol | 2.0 g. |
| | Triethanolamine 99% | 1.0 g. |
| B | Sodium lauryl sulfate | 0.25 g. |
| | Methyl p-hydroxybenzoate | 0.1 g. |
| | p-aminobenzoic acid | 5.0 g. |
| | Fragrance | 0.15 g. |
| | | 100.00 g. |

EXAMPLE VI

An insect repellent was prepared having the following formulation:

| | | |
|---|---|---|
| A | Stearic Acid | 4.0 g. |
| | Sorbitan Tristearate | 0.5 g. |
| | Cetyl Alcohol | 0.5 g. |
| | N,N-Diethyl-m-toluamide | 15.0 g. |
| | Propyl p-hydroxybenzoate | 0.1 g. |
| | Deionized Water | 77.0 g. |
| | Propylene Glycol | 1.4 g. |
| B | Triethanolamine 99% | 1.0 g. |
| | Sodium lauryl sulfate | 0.25 g. |
| | Methyl p-hydroxybenzoate | 0.1 g. |
| | Fragrance | 0.15 g. |
| | | 100.00 g. |

EXAMPLE VII

An analgesic cream was prepared having the following formulation:

| | | |
|---|---|---|
| A | Stearic Acid | 4.0 g. |
| | Sorbitan Tristearate | 0.5 g. |
| | Cetyl Alcohol | 0.5 g. |
| | Lanolin Alcohols | 2.5 g. |
| | Isopropyl Myristate | 2.5 g. |
| | Methyl Salicylate | 2.0 g. |
| | Propyl p-hydroxybenzoate | 0.1 g. |
| | Deionized Water | 85.15 g. |
| | Glycerine | 1.4 g. |
| B | Triethanolamine 99% | 1.0 g. |
| | Sodium lauryl sulfate | 0.25 g. |
| | Methyl p-hydroxybenzoate | 0.1 g. |
| | | 100.00 g. |

EXAMPLE VIII

A sun burn remedy was prepared having the following formulation:

| | | |
|---|---|---|
| A | Stearic Acid | 4.0 g. |
| | Sorbitan Tristearate | 0.5 g. |
| | Cetyl Alcohol | 0.5 g. |
| | Lanolin Alcohols | 2.5 g. |
| | Isopropyl Myristate | 1.5 g. |

-continued

|   | | |
|---|---|---|
|   | Fatty acid diester of a coconut oil derived polyol | 2.5 g. |
|   | Ethyl p-aminobenzoate | 1.0 g. |
|   | Propyl p-hydroxybenzoate | 0.1 g. |
|   | Deionized Water | 84.5 g. |
|   | Propylene Glycol | 1.4 g. |
| B | Triethanolamine 99% | 1.0 g. |
|   | Sodium lauryl sulfate | 0.25 g. |
|   | Methyl p-hydroxybenzoate | 0.1 g. |
|   | Fragrance | 0.15 g. |
|   |   | 100.00 g. |

EXAMPLE IX

A high emolliency, moisturizing cream having the following formulation is charged with the indicated propellant system:

|   | | |
|---|---|---|
|   | Stearic Acid | 4.0 g. |
|   | Sorbitan Tristearate | 0.5 g. |
|   | Cetyl Alcohol | 0.5 g. |
| A | Lanolin Alcohols | 5.0 g. |
|   | Isopropyl Myristate | 5.0 g. |
|   | Fatty acid diester of a coconut oil derived polyol | 5.0 g. |
|   | Propyl p-hydroxybenzoate | 0.1 g. |
|   | Deionized Water | 73.35 g. |
|   | 70% Sorbitol | 3.0 g. |
| B | Triethanolamine 99% | 1.0 g. |
|   | Sodium Lauryl Sulfate | 0.25 g. |
|   | Methyl p-hydroxybenzoate | 0.1 g. |
|   | Fragrance | 0.20 g. |
|   |   | 100.00 |

Heat A to 170°F. Heat B to 170°F. Add A to B with mild agitation. Continue mild stirring for 10 minutes. Force cool to 120°F. and add fragrance. Force cool to 10°F.

150 grams of the emulsion was charged to individual 6 oz. aerosol containers, pressurized and subjectively evaluated as defined in Example I with similar results.

As will be apparent to one skilled in the art, various modifications can be made in the illustrative embodiments defined hereinbefore and still fall within the scope of the present invention. For example, by varying the ratios of ingredients and selecting alternative materials for forming the emulsion matrix, as well as using different foam-forming ingredients, substantial variations can be obtained in the ultimate composition to meet specific needs. The propellant systems described herein will provide an excellent discharge rate of foam and will substantially exhaust the container without any deterioration of the desired foam characteristics. Moreover, the pressure upon storage of the container will remain substantially identical to the original charging pressure.

We claim:

1. An aerosol package containing a foam-forming, oil-in-water emulsion and a propellant system consisting essentially of nitrous oxide and isobutane, the weight ratio of nitrous oxide to isobutane being from about 2:1 to about 1:1.5.

2. An aerosol package as defined in claim 1 wherein said foam has a density from about 0.10 to about 0.18 g/cc and a stiffness from about 240 to about 350 grams/square centimeter.

3. A propellant system for use in an aerosol package containing a foam-forming, oil-in-water emulsion, said propellant system consisting essentially of nitrous oxide and isobutane, the weight ratio of nitrous oxide to isobutane being from about 2:1 to about 1:1.5.

4. A propellant system as defined in claim 3 consisting of from 0.5 to 4.0 parts by weight isobutane and 1.0 to 3.5 parts by weight nitrous oxide per 142 parts by weight of a foam forming oil-in-water emulsion.

5. A propellant system as defined in claim 3 consisting of from 1.4 to 3.5 parts by weight isobutane and from 1.5 to 2.4 parts by weight nitrous oxide per 142 parts by weight of a foam forming oil-in-water emulsion.

* * * * *

UNITED STATES PATENT OFFICE
CERTIFICATE OF CORRECTION

Patent No. 3,970,584    Dated July 20, 1976

Inventor(s) John W. Hart and Thomas C. Rolfson

It is certified that error appears in the above-identified patent and that said Letters Patent are hereby corrected as shown below:

Column 3, line 17, "exampls" should be --examples--.
Column 5, in the formula of Example I, delete lines 9-15 of the formula, and insert therefor --

|   |   | Talc | 2.00 g. |
|---|---|---|---|
|   |   | Deionized water | 8.5 45 g. |
|   |   | 70% Sorbitol | 2.00 g. |
|   | B | Triethanolamine | 1.00 g. |
|   |   | Sodium lauryl sulfate | 0.25 g. |
|   |   | Methyl p-hydroxybenzoate | 0.10 g. |
|   | C | Fragrance | 0.15 g. |

--

Column 6, line 10, "shaking" should be --"shaking"--.
Column 9, in the formula of Example IV, delete lines 5-13 of the formula, and insert therefor --

|   |   | Deionized Water | 36.5 g. |
|---|---|---|---|
|   |   | Isopropyl Myristate | 2.0 g. |
|   |   | Glycerol Monoisostearate | 0.5 g. |
|   |   | Triethanolamine 99% | 1.1 g. |
|   | B | Propylene Glycol | 1.1 g. |
|   |   | Oleyl Sarcosine | 2.1 g. |
|   |   | Super diethanolamide of lauryl acid | 3.8 g. |
|   |   | Fragrance | 0.5 g. |

--

Column 9, Table IV, the caption "Sample No." should be over the column starting "30", the caption "Propellant System (g.)" should be over the columns starting "Propellant 12" and "(11.5)".

UNITED STATES PATENT OFFICE
CERTIFICATE OF CORRECTION

Patent No. 3,970,584      Dated July 20, 1976

Inventor(s) John W. Hart and Thomas C. Rolfson

It is certified that error appears in the above-identified patent and that said Letters Patent are hereby corrected as shown below:

-Page 2-

Column 9, in the formula of Example V, delete lines 6-13 of the formula, and insert therefor --

|   |                          |         |
|---|--------------------------|---------|
|   | Propyl p-hydroxybenzoate | 0.1 g.  |
|   | Deionized Water          | 76.9 g. |
|   | 70% Sorbitol             | 2.0 g.  |
|   | Triethanolamine 99%      | 1.0 g.  |
| B | Sodium lauryl sulfate    | 0.25 g. |
|   | Methyl p-hydroxybenzoate | 0.1 g.  |
|   | p-aminobenzoic acid      | 5.0 g.  |
|   | Fragrance                | 0.15 g. --  |

Column 10, in the formula of Example VI, delete lines 5-11 of the formula, and insert therefor --

|   |                          |         |
|---|--------------------------|---------|
|   | Propyl p-hydroxybenzoate | 0.1 g.  |
|   | Deionized Water          | 77.0 g. |
|   | Propylene Glycol         | 1.4 g.  |
| B | Triethanolamine 99%      | 1.0 g.  |
|   | Sodium lauryl sulfate    | 0.25 g. |
|   | Methyl p-hydroxybenzoate | 0.1 g.  |
|   | Fragrance                | 0.15 g. -- |

Column 10, in the formula of Example VII, delete lines 7-12 of the formula and insert therefor --

|   |                          |          |
|---|--------------------------|----------|
|   | Propyl p-hydroxybenzoate | 0.1 g.   |
|   | Deionized Water          | 85.15 g. |
|   | Glycerine                | 1.4 g.   |
| B | Triethanolamine 99%      | 1.0 g.   |

UNITED STATES PATENT OFFICE
CERTIFICATE OF CORRECTION

Patent No. 3,970,584          Dated July 20, 1976

Inventor(s) John W. Hart and Thomas C. Rolfson

It is certified that error appears in the above-identified patent and that said Letters Patent are hereby corrected as shown below:

-Page 3-

Column 11, in the formula of Example VIII, delete lines 4-10 of the formula and insert therefor --

|   |   |   |
|---|---|---|
|   | Sodium lauryl sulfate | 0.25 g. |
|   | Methyl p-hydroxybenzoate | 0.1 g. --|
|   | Propyl p-hydroxybenzoate | 0.1 g. |
|   |   |   |
|   | Deionized Water | 84.5 g. |
|   | Propylene Glycol | 1.4 g. |
| B | Triethanolamine 99% | 1.0 g. |
|   | Sodium lauryl sulfate | 0.25 g. |
|   | Methyl p-hydroxybenzoate | 0.1 g. |
|   |   |   |
|   | Fragrance | 0.15 g. -- |

Column 11, in the formula of Example IX, delete lines 8-14 of the formula, and insert therefor --

|   |   |   |
|---|---|---|
|   | Propyl p-hydroxybenzoate | 0.1 g. |
|   |   |   |
|   | Deionized Water | 73.35 g. |
|   | 70% Sorbitol | 3.0 g. |
| B | Triethanolamine 99% | 1.0 g. |
|   | Sodium Lauryl Sulfate | 0.25 g. |
|   | Methyl p-hydroxybenzoate | 0.1 g. |
|   |   |   |
|   | Fragrance | 0.20 g. -- |

Column 11, line 33, delete "10°F." and insert therefor --100°F.--

Signed and Sealed this

Twenty-first Day of December 1976

[SEAL]

Attest:

RUTH C. MASON          C. MARSHALL DANN
*Attesting Officer*          *Commissioner of Patents and Trademarks*